United States Patent
Wang et al.

(10) Patent No.: US 10,228,373 B2
(45) Date of Patent: Mar. 12, 2019

(54) KIT AND METHOD FOR DIAGNOSIS, PROGNOSIS OR MONITORING OF LIVER DISEASE THROUGH MEASUREMENT OF AMOUNT OF AST

(71) Applicant: BODITECH MED INC., Chuncheon-si, Gangwon-do (KR)

(72) Inventors: Hong Tao Wang, Chuncheon-si (KR); Sang Yeol Park, Chuncheon-si (KR); Hyun Jeong Kim, Chuncheon-si (KR); Won Hee Lee, Chuncheon-si (KR)

(73) Assignee: BODITECH MED INC., Chuncheon-si, Gangwon (KR)

( * ) Notice: Subject to any disclaimer, the term of this patent is extended or adjusted under 35 U.S.C. 154(b) by 312 days.

(21) Appl. No.: 15/021,061

(22) PCT Filed: Sep. 11, 2014

(86) PCT No.: PCT/KR2014/008456
§ 371 (c)(1),
(2) Date: Mar. 10, 2016

(87) PCT Pub. No.: WO2015/037907
PCT Pub. Date: Mar. 19, 2015

(65) Prior Publication Data
US 2016/0223544 A1    Aug. 4, 2016

(30) Foreign Application Priority Data
Sep. 13, 2013  (KR) .......................... 10-2013-0110253

(51) Int. Cl.
*G01N 33/573*   (2006.01)
*C07K 16/40*    (2006.01)
*G01N 33/574*   (2006.01)

(52) U.S. Cl.
CPC ........... *G01N 33/573* (2013.01); *C07K 16/40* (2013.01); *G01N 33/57438* (2013.01); *G01N 2333/91188* (2013.01); *G01N 2800/085* (2013.01)

(58) Field of Classification Search
None
See application file for complete search history.

(56) References Cited

U.S. PATENT DOCUMENTS 7,981,627 B2    7/2011  Lederkremer
2006/0172286 A1  8/2006  Poynard

FOREIGN PATENT DOCUMENTS

KR   10-2004-0021768 A   3/2004
KR   10-0502275 B1       7/2005

OTHER PUBLICATIONS

Jeong et al. "Sandwich ELISA for Measurement of Cytosolic Aspartate Aminotransferase in Sera from Patients with Liver Diseases" ,Clin Chem. May 2003;49(5):826-9, DOI: 10.1373/49.5.826 Published May 2003.*
Wang et al. "Measurement of human aspartate aminotransferase isoenzymes in serum by immunoassay method" (Jan. 2012), Poster P028, Annual Symposium—Frontiers in Biological Catalysis, Jan. 10-12, 2012, Robinson College Cambridge, UK, https://www.biochemistry.org/Portals/0/Conferences/abstracts/SA127/SA127.*
Front matter for Wang et al. poster abstract, as retrieved from https://www.biochemistry.org/Events/tabid/379/View/Posters/MeetingNo/SA127/Default.aspx on Jun. 26, 2018, three pages (Year: 2012).*

* cited by examiner

*Primary Examiner* — Christine Foster
(74) *Attorney, Agent, or Firm* — Vorys, Sater, Seymour & Pease LLP; Mih Suhn Koh (57) ABSTRACT

Disclosed are: a kit and a method for diagnosing or monitoring a liver disease, comprising a detection reagent for one or more markers of cytosolic aspartate aminotransferase (cAST) and mitochondrial aspartate aminotransferase (mAST) as biomarkers in a biological sample; and an antibody used for the detection. Compared to the conventional enzyme activity measurement method, the method according to the present application can more accurately measure diagnosis or prognosis of a liver disease with high sensitivity through measurement of the amount of mAST or cAST present in the biological sample, in particular, in a blood sample.

4 Claims, 8 Drawing Sheets
(4 of 8 Drawing Sheet(s) Filed in Color)

KIT AND METHOD FOR DIAGNOSIS, PROGNOSIS OR MONITORING OF LIVER DISEASE THROUGH MEASUREMENT OF AMOUNT OF AST

BACKGROUND OF THE INVENTION

Field of the Invention

The present disclosure relates to diagnose of liver cancer based on the immunological detection of biomarker.

Description of the Related Art

Hepatic disease is one of the most prevalent disorders in human and there are over 100 known forms, many of which are fatal. Particularly Hepatocellular carcinoma (HCC) is the 5th leading cause of cancer related death worldwide and the death rate due to HCC is on the rise. Patients with HCC are usually asymptomatic until the later stage. Therefore, the patients can be greatly benefited by early diagnosis or detection.

Several parameters are currently used to examine the proper function of liver in clinical practice. One of them is to measure the level of Aspartate aminotransferase (AST), which is found in high concentration in hepatocytes. AST is released from hepatocytes into the blood when hepatocytes are damaged due to various factors such as toxic materials, viral infection, excess alcohol intake, and obesity. AST catalyzes reversible reactions of converting L-aspartate and α-ketoglutarate to oxaloacetate and L-glutamate, respectively and thus are used to diagnose and monitor liver disease, particularly the one resulting in a destruction of hepatocytes.

AST exists in mammalian tissues as two distinct isoenzymes, one located in the cytoplasm (cAST), and the other in mitochondria (mAST). Although there have been serval attempts, the measurement of isoenzymes has not been widely utilized for clinical diagnosis of hepatic disease. This is due to the pyridoxal-5-phosphate (co-enzyme of AST) that negatively affects the measurement leading to the inaccurate results. A typical use of AST in connection with liver disease is to measure the total enzymatic activities of both cAST and mAST. However, the test results may not represent the exact amount of AST present in tissues since they may be degraded or modified in the blood stream after they have been released into the blood.

According to the previous studies, liver, heart, skeletal muscle, kidneys, and brain are the main sources of AST and did not disclose regarding the separate distribution or presence of cAST and mAST.

KR Patent Publication No. 2002-0053113 relates to an immunological method of quantitative measurement of enzymes in serum such as AST. However, there are no mention in relation to the separate measurement of cAST and mAST for diagnosis of liver disease.

U.S. Pat. No. 7,981,627 relates to a method of monitoring and diagnosing liver cirrhosis including measuring AST level in the blood of a subject.

US Patent Publication No. 2006-0172286 relates to a method of diagnosing liver cancer including determining the activity of biomarker such as AST in the serum or blood of a subject.

However, they do not disclose measuring the cytoplasmic and mitochondrial isoforms of AST separately in connection with diagnosis of liver disease.

SUMMARY OF THE INVENTION

The present disclosure relates to a use of cAST and/or mAST to detect liver disease and thus is to provide methods, kits and compositions to detect levels of cAST and/or mAST in biological samples such as blood for diagnosis, prognosis or monitoring liver disease.

In one aspect of the present disclosure, there is provided a kit or composition of diagnosis or prognosis or monitoring liver disease comprising an agent for detecting a level of at least one of cytoplasmic aspartate aminotransferase (cAST) and mitochondrial aspartate aminotransferase (mAST) in a biological sample.

The present kits or compositions are used to analyze the present biomarkers in biological samples including for example whole blood, plasma, or serum. In one embodiment, a serum is used.

The agents that are employed in the present methods, composition or in kits are materials for quantitative or qualitative analysis. In one embodiment, the agent includes for analysis including such as a western blot, an ELISA, an radioimmunoassay, an immunodiffusion assay, a immunochromatography, an immunoelectrophoresis, an immunostaining, an immunoprecipitation, a complement fixation assay, an mass spectrometry, or a protein microarray, but does not limited thereto. In other embodiment, the agent is a monoclonal antibody, a polyclonal antibody, an antibody fragment, an aptamer, an avimer, a peptidomimetic, a receptor, a ligand or a cofactor, which specifically recognizes the cAST or mAST, but is not limited thereto.

In other embodiment, the antibody employed in the present disclosure is a monoclonal antibody deposited as KCTC 12483BP; KCTC 12484BP; and KCTC 12485BP in Korean Collection for Type Cultures.

The present kits and compositions are used for various assays to determine the presence and/or level of at least one of cAST and mAST in biological samples. Such assays include but are not limited to an ELISA, an immunochromatography or a protein microarray.

Liver disease that may be diagnosed, monitored and/or prognosis in the present kits, compositions and methods includes a hepatitis, a hepatic cirrhosis or a liver cancer but is not limited thereto. Also included are a state or a condition that is yet to be confirmed as liver disease but is suspected of liver disease.

In other aspect of the present disclosure, there is provided a method to diagnose, prognosis, or monitor liver disease based on the level and/or presence of cAST and/or mAST in a sample or a subject in need thereof. In one embodiment, the present method comprises steps of: measuring the level of at least one of cAST and mAST in a biological sample from a subject in need thereof; comparing the level of the above step to that of a control sample or to the predetermined cut-off value; and determining that the sample or the subject has a liver disease when there is a change, particularly an increase in the level compared to that of the control.

The assays which may be employed in the present methods are as described above and include for example a western blot, an ELISA, a radioimmunoassay, an immunodiffusion assay, an immunochromatography, an immunoelectrophoresis, an immunostaining, an immunoprecipitation, a complement fixation assay, an mass spectrometry, or a protein microarray, but are not limited thereto. Liver diseases that may be diagnosed with the present methods and biological samples that may be employed for the present methods are as disclosed hereinbefore.

In other aspect of the present disclosure, there is provided a method of quantitatively analyzing or detecting the level of at least one of cAST and/or mAST. In one embodiment, the method comprises steps of: providing an antibody specific to at least one of cAST and mAST; incubating the antibody with a blood from a subject; and determining the concentration of at least one of the cAST and mAST. The level of cAST and mAST may be quantitatively determined by various methods known in the art as described hereinbefore, which includes for example, a sandwich ELISA is used.

The antibody that may be employed in the present kits, compositions and methods are monoclonal antibodies. For example, anti-cAST antibody is at least one disclosed as HCC 1 to 10 in Table 1, and anti-mAST is at least one disclosed as HCM 1 to 10 in Table 1. In one embodiment, the antibody specific to cAST is HCC4 or HCC5 in Table 1, and the antibody specific to mAST is HCM 4 or HCM 8 in Table 1. In other embodiment, the antibody is a monoclonal antibody deposited as KCTC 12483BP; KCTC 12484BP; or KCTC 12485BP in Korean Collection for Type Cultures.

In other aspect, there is provided a monoclonal antibody specifically recognizing cAST deposited as KCTC 12483BP; or KCTC 12484BP deposited Sep. 4, 2013 in Korean Collection for Type Cultures. Also provided is a monoclonal antibody specifically recognizing mAST deposited as KCTC 12485BP deposited Sep. 4, 2013 in Korean Collection for Type Cultures. The antibodies of the present disclosure recognize their respective antigen, cAST and mAST, respectively, with a high specificity, and have no cross reactivity to other antigen. Thus the present monoclonal antibodies can be advantageously used to detect the presence and/or level of cAST and mAST in biological samples.

ADVANTAGEOUS EFFECTS

The present methods to diagnose or detect Chronic Hepatitis (CH), Liver Cirrhosis (LC) and/or HCC by immunologically measuring the concentration of cAST and mAST show a greater specificity compared to the conventional method of measuring the enzymatic activity. Thus the present methods can be advantageously used for diagnose, prognosis or monitor liver disease.

Also the present methods show a high sensitivity having a detection range of 0-400 µg/l of cAST and mAST. Thus, compared to the conventional method based on a biochemical assay, the present method can be advantageously used to detect even a small amount of cAST and/or mAST in the serum. The present antibodies against cAST or mAST have no cross-reactivity therebetween, and thus can be effectively used for accurate differentiation and thus accurate and separate measurement of cAST and mAST.

Compared to the conventional method in which a total amount of AST is measured, the present methods can be more effectively used in diagnosing liver disease by measuring cAST and mAST separately.

BRIEF DESCRIPTION OF THE DRAWINGS

The patent or application the contains at least one drawing executed in color. Copies of this patent or patent application publication with color drawing(s) will be provided by the Office upon request and payment of the necessary fee.

These and/or other aspects and advantages of the invention will become apparent and more readily appreciated from the following description of the embodiments, taken in conjunction with the accompanying drawings of which:

FIG. 7 is the result of analyzing cAST and mAST in serum using sandwich ELISA assay. A is the cAST result, in which monoclonal antibodies HCC4 and HCC5 were used as capture and detection antibody respectively, and cAST was used as a reference protein. The recombinant protein cAST was diluted with 1/5 normal serum (10 IU/L) and 4/5 PBS. The concentrations of the recombinant protein cAST used were 0 µg/l, 6.25 µg/l, 12.5 µg/l, 25 µg/l, 50 µg/l, 100 µg/l, 200 µg/l, 400 µg/l. B is the mAST result, in which monoclonal antibodies HCM4 and HCM8 were used as capture and detection antibody respectively, and recombinant mAST was used as a reference protein. The recombinant protein mAST was diluted with 1/5 normal serum (10 IU/L) and 4/5 PBS. The concentrations of the recombinant protein mAST used were same as above. Each spike point on the curve represents the results of three independent experiments.

DETAILED DESCRIPTION OF THE EMBODIMENTS

The present disclosure is based on the discovery that liver disease can be diagnosed by the detection of cytoplasmic aspartate aminotransferase (cAST) and mitochondrial aspartate aminotransferase (mAST) in the blood.

In one aspect, the present disclosure relates to a use of cAST and mAST as a biomarker to diagnose liver disease. In the present disclosure, there is provided a kit or composition for diagnosis, prognosis or monitoring liver disease comprising agent(s) to detect at the quantitative or qualitative level at least one of cAST and mAST.

The term "diagnosis" as used herein includes determining the disease or disorder susceptibility of a subject or whether a subject has a specific disease or disorder.

The term "prognosis" as used herein incudes determining in a subject who has a specific disease or disorder, for example, pre-transitional or transitional status of disease such as identification of stages or progression of a cancer or determining the response to cancer treatments.

The term "monitoring" as used herein includes observing a normal subject or a subject suspected of a disease has developed a disease, or therametrics (for example, monitoring the status of a subject to provide the information on the efficacy of treatment).

The biological sample of the present disclosure is a substance or a mixture of the substances that contain or is expected to contain/express one or more of the present biomarkers, and includes cells, tissues or bodily fluids from an organism, particularly human, for example, whole blood, urine, plasma, and serum, but is not limited thereto. In addition, the sample includes cells or tissues cultured in vitro as well as those derived directly from an organism. Various samples may be used for the detection of biomarkers according to the present disclosure.

In one embodiments, blood samples are used. The blood sample in the present disclosure includes a collection of similar cells obtained from the blood of subjects including patients and normal person. In addition, the blood which may be employed in the present disclosure includes fresh, frozen and/or conserved blood, or any components thereof. Also encompassed in the present disclosure are serum, plasma and whole blood.

Also encompassed in the present disclosure are blood, cells or fraction of tissues or derivative thereof. When cells or tissues are used, they may be used as it is or as a lysate thereof.

The term "liver disease" as used herein refers to a symptom or a condition due to a malfunction in all or part of liver and includes for example acute or chronic hepatitis of viral origin, liver cirrhosis, liver cancer and hepatocellular carcinoma and the like. Also encompassed in the present disclosure are the disease that is not identified with specific name, but that can be identified by having abnormal values such as in GOP, GPT, and/or γ-GTP.

The term biomarker, or diagnosis marker as used herein refers to an agent that may discriminate a diseased tissues or cells from normal cells or a treated tissues or cells, and comprises proteins, mAST and cAST. In one embodiment, the amount, concentration, or level of mAST and/or cAST is detected for diagnosis, prognosis or monitoring of liver disease.

The term detection or detecting as used herein refers to a determination in quantity, quality and/or changes in expression and/or profiles of the expression. The detection includes a determination of the presence and/or absence as well as the levels of the present markers. The present markers may be detected using the methods known in the art, and the person skilled in the art would be easily able to select appropriate methods for the detection. In one embodiment, antibodies that specifically recognize cAST or mAST of the present disclosure are used.

The kits or compositions of the present disclosure may be employed or provided for various detection methods. In one embodiment, ELISA, a dip stick rapid kit based on lateral immunochromatography, a microarray or an immunoassay.

The quantitative and qualitative analysis of the makers for diagnosis liver disease according to the present disclosure may be done by various methods known in the art that can detect proteins quantitatively or qualitatively. For example, the methods include a western blot, an ELISA, a radioimmunoassay, an immunodiffusion, an immunoelectrophoresis, an immunostaining, an immunoprecipitation, a complement fixation assay, and an array system such as protein array such as antigen array, a binding with a tailed antibody in solution/suspension or a mass spectrometry, and the like. These methods are known in the art and for example Enzyme Immunoassay, E. T. Maggio, ed., CRC Press, Boca Raton, Fla., 1980; Gaastra, W., Enzyme-linked immunosorbent assay(ELISA), in Methods in Molecular Biology, Vol. 1, Walker, J. M. ed., Humana Press, NJ, 1984; mass spectroscopy: Petricoin et al. 2002. Lancet 359: 572-77; eTag systems: Chan-Hui et al. 2004. Clinical Immunology 111: 162-174; microparticle-enhanced nephelometric immunoassay: Montagne et al. 1992. Eur J Clin Chem Clin Biochem. 30:217-22 may be referred, In one embodiment, an immunoassay using sandwich system like ELISA (Enzyme Linked Immuno Sorbent Assay), or RIA (Radio Immuno Assay) and the like may be used for quantitative and/or qualitative detection of the present markers. In this system, the biological samples are reacted with a first antibody fixed to a solid substrate/support such as a glass, a plastic (for example, polystyrene), polysaccharides, a bead, a nylon or nitrocellulose membrane or a microplate well to form a complex and the complex is then allowed to react with an second antibody that is usually labeled with agents that can be detected directly or indirectly such as radioactive substances like $^3$H or $^{125}$I, fluorescent materials, chemiluminescent substances, hapten, biotin, or digoxygenin and the like. In some cases, the labeling materials are conjugated with an enzyme such as horseradish peroxidase, alkaline phosphatase, or maleate dehydrogenase that is able to produce colors or color changes or illuminate in the presence of appropriate substrates.

Other methods based on immune reaction may also be used. In other embodiment, Immuno Electrophoresis methods that can detect biomarker based on an antigen-antibody reaction such as an Ouchterlony plate, a Western blot, a Crossed IE, a Rocket IE, a Fused Rocket IE, or an Affinity IE; a radioimmunoassay; an immunodiffusion; an immunoelectrophoresis; an immunostaining; an immunoprecipitation; mass spectrometry; a protein microarray; or a complement fixation assay may be used.

The compositions and kits of the present disclosure may comprise various detection agents depending on the particular methods employed. For example, detection agents such as to determine the level (concentration) of protein and/or the presence of biomarker.

In one embodiment, the detection agents include antibodies, antibody fragments, substrates, aptamers, avimers or peptidomimetics, or receptors or ligand or cofactors that specifically interact with the present biomarkers.

In other embodiment, the detection agents include agents used for Western blot, ELISA, radioimmunoassay, immunodiffusion assay, immunoelelctrophoresis, immunohistochemistry, immunopercipiation, complement fixation assay, mass spectrometry, or protein array system.

The agents or materials used for the methods as described herein are known in the art. The present biomarkers may be detected based on an antigen-antibody reaction, or a reaction with a substrate, peptide aptamer, receptor, ligand or cofactor specifically recognizing the present biomarker or by mass spectrometry.

The agents or materials that specifically bind or interact with the present biomarker may be used in a chip based assay or with nanoparticles.

In one embodiment, immunoassays employing monoclonal antibodies are used. Monoclonal antibodies may be prepared by methods known in the art, for example by fusion methods (Kohler and Milstein, European Journal of Immunology, 6:511-519(1976)), recombinant DNA technology (U.S. Pat. No: 4,816,56$\overline{\text{7}}$.) or phage antibody library methods (Clackson et al, Nature, 352:624-628(1991) and Marks et al, J. Mol. Biol., 222:58, 1-597(1991)). Genera procedure for preparing antibody may be found in Harlow, E. and Lane, D., Using Antibodies: A Laboratory Manual, Cold Spring Harbor Press, New York, 1999; Zola, H., Monoclonal Antibodies: A Manual of Techniques, CRC Press, Inc., Boca Raton, Fla., 1984; and Coligan, CURRENT PROTOCOLS IN IMMUNOLOGY, Wiley/Greene, NY, 1991). For example, the preparation of hybridoma cells producing monoclonal antibodies may be performed by fusing immortal cell lines with antibody producing lymphocytes, the process of which is known in the art and may be practiced by one of ordinary skill in the art without difficulty.

In other embodiment, immunoassays employing anyone of antibodies as listed in Table 1 named as HCC 1 to 10 for cAST, and HCM 1 to 10 for mAST. The antibodies according to the present disclosure are prepared by injecting purified cAST and mAST recombinant protein into balb/c mouse followed by cell fusion and screening to select hybridoma cells producing monoclonal antibody. The purified monoclonal antibodies are characterized and grouped as a sandwich match pairs. It is preferred that there are no cross reactivity between anti-cAST and anti-mAST antibodies. The match pairs among antibodies listed in Table 1 may be selected by characterizing the antibodies using indirect ELISA, antibody isotyping and/or western blot. In one embodiment, as a match pair antibody, HCC4 or HCC5 as anti-cAST monoclonal antibody, and HCM4 or HCM8 as anti-mAST monoclonal antibody are used, but is not limited thereto.

In this perspective, there is provided a monoclonal antibody specifically recognizing cAST, which is deposited as KCTC 12483BP on Sep. 4, 2013, in KCTC.

In other perspective, there is provide a monoclonal antibody specifically recognizing cAST, which is deposited as KCTC 12485BP on Sep. 4, 2013, in KCTC.

The present kit and composition may be employed in various detection methods. For example the kit or composition may be provided or formulated as ELISA kit, immunochromatography strip kit, chemiluminescence kit and Luminex® kit.

In one embodiment, the present method, kit and composition are used for ELISA, in which antibodies specific for the present biomarkers are used. The antibodies employed in the present disclosure specifically recognize the present biomarker and have high affinity without cross-reactivity to other biomarkers, which includes monoclonal antibodies, polyclonal antibodies or recombinant antibodies. In addition, when ELISA are used for the detection of present marker, antibodies specific to controls may also be utilized. Others reagent to detect the capture antibodies such as labelled secondary antibody, chromophores, enzyme conjugated with antibody and its substrate or any material that can bind to an antibody and the like may also be used.

In other embodiment, the present kit, composition or method may also be employed in Luminex® methods.

The Luminex® kit, as a high-throughput quantitative analysis method capable of simultaneously measuring a maximum of 100 different kinds of analytes employing a small amount (10 to 20 µl) of biological samples which are not pre-treated, is an analysis method having a high sensitivity (pg unit) and short analysis time, and can replace an existing ELISA or ELISPOT. The Luminex® assay, as a multiplex fluorescence microplate assay capable of simultaneously measuring more than 100 different kinds of biological materials in each well of a 96-well plate, distinguishes and quantifies more than 100 different color groups of polystyrene beads by performing signal transfer in real time by using two kinds of laser detectors. The 100 beads may be constituted to be distinguished such that at one side, red fluorescence beads are divided into 10 different levels of fluorescent intensity and at the other side, orange fluorescence beads are divided into 10 different levels of intensity. Further, the beads therebetween have a unique intensity according to the mixed ratio of the orange and red fluorescence thus generating 100 color-coded bead set. Further, an antibody specific to the maker to be analyzed is attached to each bead and thus the biomarkers may be quantified by an immune antibody reaction using the beads The kit capable of performing the Luminex® assay of the present disclosure includes a specific antibody to the biomarker. The antibody employed has a high specificity and affinity to each biomarker and almost no across-reactivity against other biomarkers. Such antibodies are a monoclonal antibody, a polyclonal antibody, or a recombinant antibody. Further, the Luminex® kit may also include a specific antibody to a material in a control group. Other Luminex® kits may also include reagents capable of detecting the antibody bound to the marker, for example, labelled secondary antibodies, chromophores, enzymes (for example, conjugated to antibodies), and substrates thereof or other materials capable of binding to antibodies. The antibody may be an antibody conjugated to microparticles and further, the microparticle may be colored latex or a colloidal gold particle.

In other embodiment, the kit of the present disclosure is used as a rapid test kit including such as an immunochromatographic strip in dip stick format for diagnosis or detection. For this the kit includes essential elements required for performing a rapid test which may show the results within 5 minutes. The immunochromatographic strip may include (a) a sample pad to which a sample is absorbed; (b) a binding pad in which binding reaction with a biomarker of interest in samples occurs; (c) a reaction membrane on which a reaction line including monoclonal antibodies for the biomarker and a control line are formed; (d) an absorption pad to which the residual sample is absorbed; and (e) a backing or supporting material. The antibody employed has a high specificity and affinity to each biomarker and almost no across-reactivity against other biomarkers. Such antibodies are a monoclonal antibody, a polyclonal antibody, or a recombinant antibody. Further, the rapid test kit may include an antibody specific to a control material. Other rapid test kits may include other materials required for diagnosis such as reagents capable of detecting the bound antibodies, for example, a nitro cellulose membrane to which the specific antibody and the secondary antibody are fixed, a membrane coupled with the beads bound to the antibody, the absorption pad, and the sample pad. In one embodiment, antibodies according to the present disclosure are used.

The present kit can be used for diagnose, monitor and/or prognosis of liver disease. Further, by determining whether the amount of corresponding biomarkers in a patient with liver disease is returned to a normal range after the treatment, it is possible to determine and monitoring the efficacy of the therapy used.

In this perspective, there is provided a method for detecting the biomarker for specific for liver cancer in a subject or in a sample in need thereof using the present kit or composition to provide information to diagnose, monitoring and/or prognosis liver disease.

In one embodiment, the present methods comprise steps of determining the presence or the level of at least one of cAST and/or mAST in a biological sample in need thereof and from a control sample; and comparing the results from the above step to that of a corresponding marker determined from the control sample; and diagnose or determine that the subject or a sample as liver cancer when there are changes in the level or in the presence of the biomarker in the subject or the sample compared to the control sample.

The term "subject" as used herein refers to any single individual that requires treatment including human beings, cattle, dogs, guinea pigs and rabbits. Also included are any subjects who do not show clinical symptoms and participate in clinical studies, or any subjects who participate in epidemiology test or are used as controls.

In the present methods, the biomarkers can be analyzed in quantitative and qualitative way. And by comparing the analysis result with that from controls, the present methods can be advantageously used for diagnose, monitor or prognosis of liver cancer, or determine the stage of liver disease.

According to one embodiment, the levels of cAST and/or mAST are determined by immunological methods in serum samples from a subject; and the measured values are used to diagnose, monitor and/or prognosis of liver cancer.

By way of examples, the cut off (upper limit in the case of biomarker the level of which increases in a sample suspected of the disease) value for a particular marker may be determined in reference to the values determined in a control group. The cut off value is then used for diagnosis of the subject suspected of the disease and the subject may be diagnosed as having liver disease when the value is increased about 50% or more, about 100% or more compared to cut off value. However, the value is not limited thereto, and it may vary depending on the type of specific regents and/or samples and/or methods employed for the analysis. Thus, specific values may be determined in consideration of the factors as described above. In addition, by determining whether the level of the corresponding biomarkers in a patient with liver disease is returned to a normal range after treatment, it is possible to determine and monitoring the efficacy of the therapy used.

The present methods may be used alone or in combination with conventional methods. For example, to diagnose, prognosis or monitor or to provide information therefor, in addition to the blood analysis, other clinical information may also be used. Other clinical information includes for example patient's age, sex, body weight, diet habit, or body mass index, or information from ultrasound, Computer Tomography, MRI, angiography, Endoscopic Retrograde Cholangio-Pancreatography, endoscopic ultrasound, cancer markers or celioscope.

The present disclosure is based on measuring the level of cAST and mAST to detect damaged liver in the blood.

In this perspective, the present disclosure relates to measuring the concentration of cAST and/or mAST in biological sample, particularly in the blood, for example, whole blood, serum or plasma.

According to one embodiment, the present method comprises steps of providing monoclonal antibody(ies) that specifically recognize at least one of mAST and cAST; perform a reaction with a blood sample from a subject in need thereof and the antibody(ies); and determine the amount or concentration of mAST and/or cAST in the blood The antibodies and other agents employed in the methods are as described above.

The present disclosure is further explained in more detail with reference to the following examples. These examples, however, should not be interpreted as limiting the scope of the present invention in any manner.

EXAMPLES

Materials

For protein purification, Ni-NTA agarose was purchased from Qiagen (Germany), 6× his-tag antibody was purchased from Takara (Japan). For the production of monoclonal antibodies, complete Freund's adjuvant and incomplete Freund's adjuvant were purchased from life technologies (U.S.A.). Fetal bovine serum (FBS) and Dubellco's Modified Eagle's medium powder were purchased from Invitrogen Corporation (U.S.A.). For western blot, ECL plus western blotting detection system was purchased from Amersham Biosciences (Sweden). X-Omat AR film was purchased from Kodak (USA). For isotypes of antibodies, Immunopure monoclonal Antibody Isotyping Kit I was purchased from Pierce (U.S.A.). For enzyme activity, GO and GP-Transaminase Kit was purchased from Sigma diagnostics Inc (U.S.A.). For immunofluoresence microscopy, coverslip and slide were purchased from Fisher Scientific (USA). Fluorescent mounting medium was purchased from Dako (Denmark).

Example 1

Purification of Aspartate Aminotransferase 1-1. Expression and Purification of Aspartate Aminotransferase Human liver cytosolic aspartate aminotransferase (cAST) and mitochondrial aspartate aminotransferase (mAST) mRNAs were isolated from human liver tissue and cDNAs were synthesized from the mRNA by RT-PCR, the product of which were then cloned into a TOPO® TA cloning vector (ThermoFisher Scientific, U.S.A.) and then into a pET21a (+) vector containing 6× his tag sequence (Novagen, U.S.A.). Then the cAST and mAST recombinants were expressed under the conditions (OD value: 0.5-0.7; IPTG:

0.1 mM; incubation time: 3 hr, temperature: 37° C.) and purified by Ni-NTA resin. The purified proteins were confirmed by western blot.

Figure 1:
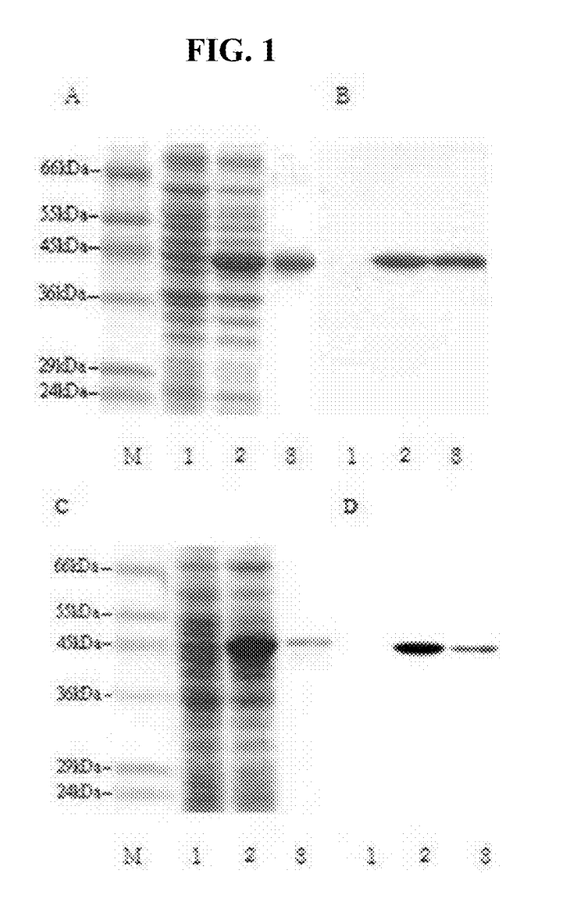
FIG. 1 is the results of 12% SDS-PAGE (A and C) and western blot analysis (B and D) of the purified recombinant cAST and mAST prepared in the present disclosure, in which the recombinant proteins having six histidine tag were induced by adding IPTG and the western blot was performed using mouse anti-his tag IgG. In the gel, Lane 1: no induction; Lane 2: Induction; Lane 3: purified after induction.

Human gene for cAST is 1,245 bp in length encoding 414 amino acids with a molecular weight of about 45 kDa. Human gene for mAST is 1,293 bp in length encoding 430 amino acids with a molecular weight of about 47 kDa. The recombinant proteins were confirmed by western blot using anti-his tag IgG as a first antibody. Results are shown in FIG. 1.

1-2. Enzyme Activity of cAST and mAST Recombinant Proteins

Human cAST and mAST are a homodimeric enzyme catalyzing the conversion of acetate and alpha-ketoglutarate to oxaloacetate and glutamate, or catalyzing the reverse reaction. The activity of the recombinant proteins were tested using a kit (Sigma, U.S.A.) using manufacturer's instruction. The activities of recombinant cAST and mAST were determined to be 1086 IU/mg and 843 IU/mg, respectively.

Example 2

Production of Monoclonal Antibodies

Immunization, cell fusion and screening hybridoma cells were performed by the methods as described below. Briefly, 6-8 weeks old Balb/c mice were injected with a purified recombinant cAST or mAST. Then the cell fusion and screenings were performed to select a total of 20 monoclonal hybridoma cell lines of cAST and mAST. Then the cells from 20 cell lines were peritoneally injected into a mouse (6-8 weeks of Balb/c), from which ascites are retrieved. The ascites were purified to recover 20 monoclonal antibodies. Anti-cAST antibodies were named as HCC 1 to HCC 10, and anti-mAST monoclonal antibodies were named as HCM 1 to HCM 10.

2-1. Complete and Incomplete Dulbecco's Modified Eagle Media (DMEM) Preparation

Two bags of powdered medium was dissolved in about 1700 ml of double distilled water (DDW) and used DDW to wash the bags to make sure all powder was dissolved in the DDW, and then 7.4 g of sodium bicarbonate was added to the solution. The medium was adjusted to pH 6.9 by 0.5 N HCl, made up to 2,000 ml, and sterilized by passing through a 0.45 µm-size filter-sterilizing unit in clean bench. Four sterilized bottles were added 450 ml of medium, 50 ml of fetal bovine serum (FBS) and 5 ml of stock solution of penicillin-streptomycin, this medium was complete Dulbecco's modified Eagle Medium (complete DMEM); One bottle was added 200 ml sterilized medium, this medium was called incomplete Dulbecco's modified Eagle Medium (incomplete DMEM). These media were stored in 4° C.

2-2. Preparation and Injection of Antigen

The recombinant cAST and mAST proteins were purified as described above. 6 to 8 weeks old Balb/c mice were immunized intraperitoneally with 0.3 ml of cAST and mAST (150 µg) separately emulsified with an equal volume of complete Freund's adjuvant. The first injection was followed by three or four booster injections of the same amount of immunogen emulsified with incomplete Freund's adjuvant at 2 to 3 week intervals. Serum was taken from the tail of the mouse and tested for antibody titer usually after the third injection. The final booster without Adjuvant was given 3 or 4 days before the cell fusion.

2-3. Preparation of Cells for Fusion 2-3-1 Preparation of Myeloma Cells

Four days before the cell fusion, frozen SP2/O cells were removed from a liquid nitrogen tank and thawed in a water bath at 37° C. as fast as possible, 30 ml of incomplete DMEM was added into the thawed cells, then the cells were spun down for 1 min at 1500 rpm, then decanted the incomplete DMEM and suspended in complete DMEM, and transferred into 75 ml flask and grown at 37° C. in 5% $CO_2$ incubator. The cells were passaged every other day. When the cell fusion was done, the SP2/O cells were transferred into 50 ml sterile tube and spun down for 1 min at 1500 rpm, decanted all supernatant and suspended the pellet with 20 ml of incomplete DMEM. For each fusion experiment, $5 \times 10^7$ cells were used.

2-3-2 Preparation of Feeder Cells

The feeder cells were prepared one day before cell fusion. A 12 to 18 weeks old mouse (any mouse strain) was sacrificed by cervical dislocation after annihilation with $CO_2$ exposure and swabbed thoroughly with 70% ethanol, and its abdominal skin was carefully removed. Five ml of ice-cold 11.6% sucrose solution was injected into the peritoneal cavity, about 4 ml of the injected solution was obtained, and peritoneal cells were collected by centrifugation for 1 min at 1500 rpm. Cells were suspended in 60 ml of complete DMEM (50× HAT was added) and added 2 drops of solution into each well of 96 well cell culture plate, usually, five plates were needed. If the feeder cells were contaminated with red blood cells, a new preparation was made. The feeder cells were cultured in 5% $CO_2$ incubator at 37° C.

2-3-3 Preparation of Spleen Cells

A mouse injected with the antigens was sacrificed by cervical dislocation after annihilation by $CO_2$ exposure and swabbed thoroughly with 70%° C. ethanol. Sterile scissors and forceps were used to incise the skin along the mid-line of the thorax up to the neck, and the fat was removed from outside of the spleen and then the spleen was placed in a sterile Petri dish containing 10 ml of incomplete DMEM. Spleen cells were then released into the medium by tearing the spleen with fine forceps and the cells were placed in a sterile 15 ml centrifuge tube.

2-3-4 Cell Fusion Procedure

The prepared spleen and SP2/O cell suspensions were combined together and spun down for 1 min at 1500 rpm. Then the supernatant was completely removed by inverting the centrifuge tube. Then the cell pellet was mixed by tapping the tube and 1 ml of 50% PEG 1500 was added slowly to the tube over a period of 90 seconds with constant swirling at 37° C. The fusion process was allowed to continue for another 90 seconds at 37° C. Exactly 3 min after adding the first drop of PEG solution, the fusion reaction was stopped by adding complete DMEM. In order to avoid an osmotic shock, 10 ml of complete DMEM was added slowly for the first minute, for a period of 1.5 min, a total of 30 ml of complete DMEM was added. Cells were then collected by centrifugation for 1 min at 1500 rpm and all the supernatant was removed. Then the pellet was suspended in 60 ml of HAT complete DMEM. Two drops of this cell suspension were added into each well of the prepared plates containing feeder cells. Then the cells were cultured at 37° C. in 5% $CO_2$ incubator.

Six days after cell fusion, the culture supernatant was removed by aspiration and two drops of HAT complete DMEM were added into each well. Hybridoma colonies were detected starting from 4 days after the fusion on an inverted microscope, and then the cells were used for screening for antibodies one day after changing medium.

2-3-5 Screening of Hybridoma Colonies

The indirect enzyme-linked immunosorbent assay (ELISA) was performed to screen hybridoma colonies. The antigen was diluted to a final concentration of 2 μg/ml in PBS and 50 μl of the diluted antigen was added to each well of a RIA plate. Then the plate was covered and incubated for 2 h at 37° C. in an incubator, or 4° C. overnight. Coating solution was decanted and the plate was washed for three times by with PBST (0.3% Tween20 in PBS). Then the remaining protein-binding sites in the coated wells was blocked by adding 300 μl blocking buffer (11.1 ml of 45% gelatin, 25 g sucrose and 1 ml of 10% sodium azide solution in 500 ml of PBS, filtered by 5 μm filter membrane) per well. The plate was incubated for 1 hour at 37° C. The plate was washed three times with PBST. 50 μl of cultural supernatant of hybridoma cells was added into each well of the plate and incubated for 1 h at 37° C. in incubator, and the plate was washed three times with PBST. Then 50 μl of horseradish peroxidase (HRP) conjugated secondary antibody was diluted at the optimal concentration (according to the manufacturer) in dilution buffer (11.1 ml of 45% gelatin and 1.5 ml of Tween 20 in 500 ml of PBS, filtered by 5 μm filter membrane) immediately before use. The plate was covered with an adhesive plastic and incubated for 1 h at 37° C. in incubator. The plate was washed three times with PBST, and 50 μl of substrate 3,3',5,5'-Tetramethylbenzidine (TMB) was added and incubated for 15 min at room temperature. 50 μl of stop solution (0.2 N sulfuric acid) was then added into each well. OD was read by a microplate reader.

Positive clones were then transferred to 24-well plates and 1 ml of HT complete DMEM was added to each well. Two days later, the clones were screened by indirect ELISA described as above. Positive clones were transferred to 6-well plates and finally grown in tissue culture flasks (75 cm$^2$) and frozen in liquid nitrogen. All the positive clones were frozen and thawed before cloning.

2-3-6 Freezing Cells

Cells grown in a culture flask (75 cm$^2$) were harvest and collected by centrifugation for 1 min at 1500 rpm and the supernatant was removed completely. The cells were suspended in 1 ml of freezing medium (90% FBS mixed with 10% dimethyl sulfoxide (DMSO)) and transferred to a freezing vial. The vial was put into NALGENE™ Cryo 1° C. freezing container and placed in a deep freezer (−70° C.) for 2 h. Then the vial was kept in a liquid nitrogen tank. It was found that the cells placed in a deep freezer for more than 3 h have low viability when thawed.

2-3-7 Cloning by Limiting Dilution

Hybridoma cells in a log phase of growth were diluted with PBS, and cell numbers were determined using a Neubauer cell counter and adjusted to 15 cells per ml by serial dilutions with HT complete DMEM. Two drops of the cell suspension were applied with a 10-ml pippet into each well of 96-well plates containing 100 μl of feeder cells prepared one day before a limited dilution. After 6 days, the supernatant of each well was exchanged with 100 μl of HT complete DMEM. The next day, indirect ELISA was used to screen the hybridoma cells. Positive colonies were selected and transferred to 24-well plate. Two days later, the clones were screened and positive clones were selected for a second limited dilution. Finally, the positive clones were frozen in a liquid nitrogen.

2-3-8 Production of Ascites Fluids

In order to induce tumors, BALB/c mice were first injected with 0.5 ml of pristane. One week later, 1×10$^7$ cells in 0.5 ml sterilized PBS were intraperitoneally injected into a mouse. Usually a swollen abdomen is noticed after a week. The mouse was then anesthetized with metofane for 3 min in a can, and the ascites fluid was collected in a 50-ml centrifuge tube by inserting a 18-gauge needle into mouse's abdomen. Finally, the mouse was sacrificed by cervical dislocation. The tube was allowed to stand for 30 min at room temperature and centrifuged for 10 min at 3000 rpm. The supernatant was removed into a fresh 15-ml tube and 0.2% sodium azid was added and stored at −20° C.

2-3-9 Purification of Monoclonal Antibody from Ascites Fluids

For purification of mAbs, 3 ml of ascites fluids were centrifuged for 20 min at 3,000 rpm, and the supernatant was diluted 2 times with PBS. Monoclonal antibodies (mAbs) were precipitated by adding an equal volume of saturated ammonium sulfate and mixed for 30 min with a gentle stirring, and the solution was centrifuged for 20 min at 15,000 rpm. The pellet was suspended in 3 ml of PBS and dialyzed against PBS four times, changed PBS every 4 h. A column was prepared, and 5 volume of 0.1M glycine (pH 2.6) was used to wash protein G after protein G sludge was applied into the column (1-ml packed volume). Then the column was extensively washed with phosphate buffer (50 mM phosphate, 500 mM NaCl, pH 6.0). The dialyzed solution was centrifuged for 30 min at 15,000 rpm to remove insoluble aggregates and the supernatant was applied to the column, and the flow through was allowed to flow slowly. The column was extensively washed with the same phosphate buffer described above and antibodies were eluted with 0.1M glycine (pH 2.6). The eluted antibody was neutralized with the addition of 0.5M Sodium phosphate (dibasic). The antibodies were dialyzed against PBS. The concentrations of mAbs were tested by Bradford test.

Example 3

Characteristics of Monoclonal Antibodies

The antibodies prepared as in Example 2 were characterized. cAST and mAST monoclonal antibodies produced from the monoclonal hybridoma cell lines were named as HCC1-HCC10 and HCM1-HCM10, respectively. Indirect ELISA, antibody isotyping and western blots were performed.

Results are shown in Table 1. Among 10 monoclonal antibodies, two monoclonal antibodies HCC4 and HCC5 were selected as optimal match pair to detect cAST, where HCC4 was used as a capture antibody and HCC5 was used as a detection antibody. In the case of mAST, HCM4 and HCM8 were selected as a capture antibody and a detection antibody, respectively. The four antibodies were then used in this Example. The cAST monoclonal antibody HCC4 (cAST 1A2C6), HCC5 (cAST, 5C3F8) were deposited as KCTC 12483BP and 12484BP, and mAST antibody HCM4 (mAST, 2E6D1) was deposited as KCTC 12485BP Sep. 4, 2013 in in Korean Collection for Type Cultures.

TABLE 1

Characteristics of monoclonal antibodies prepared in the present disclosure

| No | Activity | Western blot | Isotype |
|---|---|---|---|
| HCC1 | ++++ | ++ | IgG1 |
| HCC2 | ++ | ++ | IgG1 |
| HCC3 | +++ | ++ | IgG2a |
| HCC4[a] | +++ | + | IgG1 |
| HCC5[b] | +++ | ++ | IgG2b |
| HCC6 | +++ | ++ | IgG1 |

TABLE 1-continued

Characteristics of monoclonal antibodies prepared in the present disclosure

| No | Activity | Western blot | Isotype |
| --- | --- | --- | --- |
| HCC7 | ++++ | + | IgG2b |
| HCC8 | +++ | ++ | IgG1 |
| HCC9 | ++ | ++ | IgG2a |
| HCC10 | +++ | + | IgG1 |
| HCM1 | ++ | ++ | IgG1 |
| HCM2 | +++ | ++ | IgG1 |
| HCM3 | + | + | IgG1 |
| HCM4[c] | +++ | ++ | IgG2a |
| HCM5 | +++ | ++ | IgG1 |
| HCM6 | ++ | + | IgG1 |
| HCM7 | +++ | + | IgG2b |
| HCM8[d] | +++ | ++ | IgG1 |
| HCM9 | + | + | IgG2a |
| HCM10 | +++ | + | IgG1 |

In Table 1, the term HCC indicates anti-cAST antibodies, and HCM indicates anti-mAST antibodies; a and b indicate a capture and a detector, respectively, used in cAST ELISA, respectively; c and d indicate a capture and a detector, respectively, used in mAST ELISA.

3-1. Titer of Monoclonal Antibodies

The titer of purified Abs was tested by indirect ELISA, which was done in the same way as described above except that the first Abs were changed from culture supernatant to purified Abs (2 μg/ml).

3-2. Isotypes of mAbs

The isotypes of mAbs were determined by ImmunoPure Monoclonal Antibody Isotyping Kit according to the manufacturer's instruction.

3-3. Western Blot Analysis

Proteins were separated by SDS-PAGE. In this Example, semi-dry transfer was used to transfer proteins from a gel to a nitrocellulose membrane. Twenty minutes before SDS-PAGE was finished, four pieces of filter papers and a piece of nitrocellulose membrane were submerged into transfer buffer (50 mM Tris,40 mM glycine, 0.04% SDS, 10% Methanol), when the SDS-PAGE was finished, and the gel was put on the nitrocellulose membrane, and proteins were transferred to nitrocellulose membrane for 35-40 min at 120 mA, TBST (10 mM Tris,150 mM NaCl 0.3%, Tween®20) was used to wash the membrane once and the blot was blocked with a blocking buffer (10 mM Tris, 150 mM NaCl 0.05% Tween 20, 5% skin milk, pH8.0) for 1 h. After washing the membrane with TBST for 3 times with a 10 min interval, the blot was incubated with primary mAbs solution (0.2-1 μg/ml) for 1 h at room temperature or overnight at 4° C. and washed 3 times with TBST with a 10 min interval. The blot was treated with HRP-conjugated goat anti-mouse IgG for 1 h at room temperature and washed 3 times with TBST at 10 min interval. The blot was incubated in chemiluminescent reagent (supersignal chemiluminescent substrate, Pierce) for 5 min and transferred to a cassette and exposed for 1 min. The film was developed in a developing reagent and fixed in a fixation reagent.

3-4. The Specificity of Anti-cAST and Anti-mAST Antibodies

Figure 2:
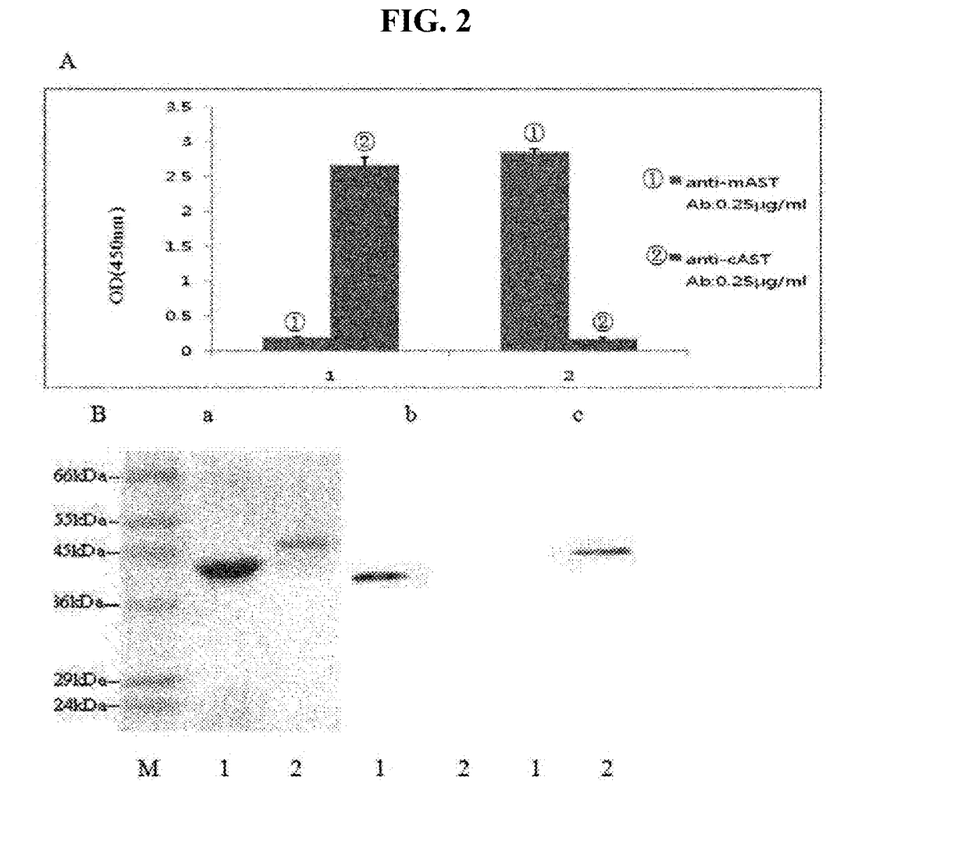
FIG. 2 is the results of analyzing the cross reactivity between anti-cAST and anti-mAST. (A) is ELISA results in which plates were coated with antigen, cAST and mAST and anti-mAST(HCM4) and anti-cAST(HCC4) were used as a primary antibody: 1: cAST coating; 2: mAST coating. (B) is results of western blot analysis in which a: SDS-PAGE; b: primary antibody HCC4; c: primary antibody HCM4. In the gel, Lane 1: cAST; Lane 2: mAST. The results show that there are no cross reactivity between anti-cAST and anti-mAST.

Human Aspartate aminotransferase isoenzymes are encoded by two different genes, but the amino acid sequence of these two enzymes has about 46% identity. Thus, it is possible that anti-cAST Abs bind to mAST protein, and anti-mAST Abs bind to cAST. In order to test the cross-reactivity of anti-cAST and anti-mAST antibodies, indirect ELISA and Western blot were performed. Results are shown in FIG. 2. In FIG. 2, (A) is a result of indirect ELISA in which antigens cAST and mAST were coated onto a plate and anti-cAST (HCC4) and anti-mAST (HCM4) were used as a primary antibody: 1: cAST coating; 2: mAST coating. (B) is a western blot analysis in which a: SDS-PAGE; b: primary antibody HCC4; c: primary antibody HCM4; 1: cAST coating; 2: mAST coating. The results show that there are no cross reactivity between anti-mAST and anti-cAST antibodies.

3-5. Peptide Mapping 30 ml of recombinant protein solution (0.1 mg/ml, 0.45% tween 20, 0.5% TRITON™ X-100 (4-(1,1,3,3-Tetramethyl-butyl)phenyl-polyethylene glycol)) was added into 1.5 ml tube, and 0.1 μl of protease (QIAGEN) was added into the solution and mixed by pipetting. The mixture was incubated for 10 min at 37° C., and 2× treatment buffer was added thereto and boiled it for 5 min. Then, 3 μl of solution was loaded into each well of a SDS-PAGE. Then western blot was performed as described in Example 3-3.

Figure 3:
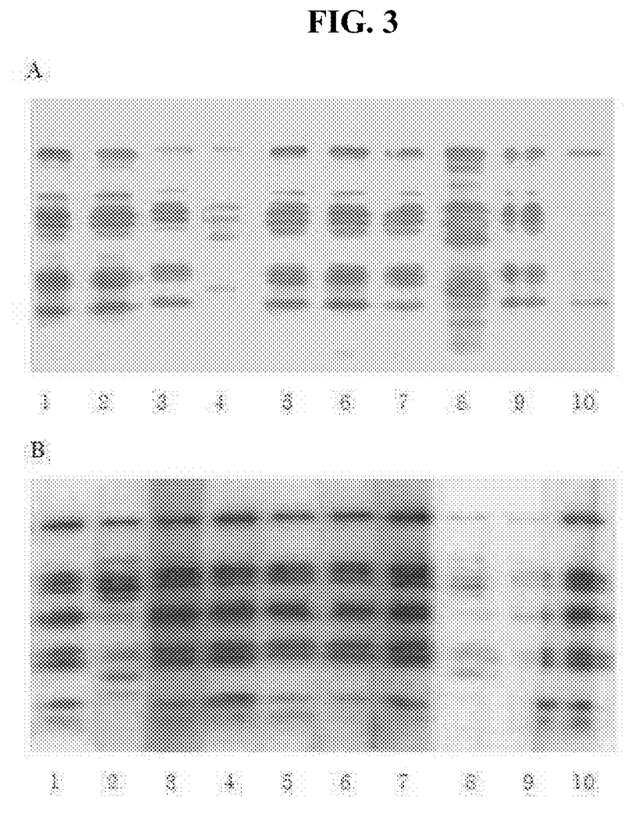
FIG. 3 is the results of peptide mapping of cAST and mAST, in which the purified recombinant cAST and mAST proteins were digested with protease and analyzed by western blot to confirm whether the monoclonal antibodies according to the present disclosure recognize the same epitopes. In the figure, A indicates cAST results, in which Lanes 1 to 10 indicate HCC1 to HCC10 used as a primary antibody, respectively. B indicates mAST results, in which lanes 1 to 10 indicate HCM1 to HCM10 used as a primary antibody, respectively.

Results are shown in FIG. 3. Monoclonal antibodies to cAST (FIG. 3, A) were found to be divided into 4 different groups. HCC1, HCC2, HCC3, HCCS, HCC6, HCC7 and HCC9 belong to one group. Each of HCC4, HCC8 and HCC10 represents one group. This indicates that HCC4 and HCCS recognize different peptide fragments, HCC4 and HCC5 bind different epitopes and can be used as a pair in an immunological sandwich assay.

Monoclonal antibodies to mAST (FIG. 3, B) were found to be divided into 2 groups. HCM1, HCM3, HCM4, HCMS, HCM6, HCM7, HCM9 and HCM10 showed the same immunological staining pattern indicating they belong to one group. HCM2 and HCM8 forms another group. This indicates that HCM4 and HCM8 belong to two different group thus they can be used as a pair to test mAST in human serum in an immunological sandwich assay.

Example 4

Specific Binding of Anti-cAST and Anti-mAST to cAST and mAST, Respectively 4-1. Conjugation of mAb with Colloidal Gold The pH of colloidal gold solution was adjusted to pH 9 with 0.05 M Borax-boric acid buffer (pH 9.0). The optimal ratio of colloidal gold solution to mAb was determined. 10 ml of colloidal gold solution (pH9.0) was mixed with mAb solution while stirring for 15 min at room temperature. The 10% BSA was added at the final concentration of 1% and the solution was stirred for 15 min. Then the solution was centrifuged for 30 min at 9000 rpm at 4° C., the supernatant was removed and the same volume of buffer (25 mM Tris-Cl, 1% BSA, 0.02% NaN$_3$, filtered by 0.2 μm-size filter) was added to suspend the pellet. The solution was centrifuged for 30 min at 9000 rpm at 4° C., and the supernatant was removed, and the same volume of buffer was added and the same procedure was repeated described as above. 1 ml of buffer was added to suspend the pellet and stored in refrigerator at 4° C. until use.

4-2. Determination of mAbs Binding to Recombinant cAST and mAST, and cAST and mAST in Serum by Colloidal Gold Conjugates, Respectively 50 μl of colloidal gold conjugated with mAb was added into each of six 1.5 ml-eppendorf tubes, and 50 μl of recombinant cAST in different concentrations of solutions or serum diluted by PBS were added into each of the six tubes. The solution was mixed by tapping the tube and incubated for 2 h at 37° C. in incubator. The tubes were centrifuged for 30 min at 9000 rpm, and the supernatant was removed. The pellet was suspend with PBS, and centrifuged for 30 min at 9000 rpm. The pellet was diluted by adding 200 µl of substrate of aspartate aminotransferase, and the solution was transferred into 15 ml tube and incubated for 1 h at 37° C. in incubator. 200 µl of the color development reagent was added into the reaction solution to develop color and incubated for 20 min at room temperature. Then 2 ml of 0.4 N NaOH was added into the solution to stop reaction. The ultraviolet spectrophotometer was used to read OD. The same experiments were done with recombinant mAST and cAST in serum.

4-3. Determination of Activities of AST Isoenzymes in Human

The serum sample used in this study was obtained from the liver cancer patient (Chronic viral hepatic cirrhosis (CVH), Liver cirrhosis (LC), and Hepatocellular carcinoma (HCC)) who enrolled in Hallym hospital under informed consent. The serum was stored at −70° C. until use. The immunoprecipitation was performed to test the activities of cAST and mAST in serum. Two tubes containing 50 µl of protein G sepharose beads (Sigma) were mixed with 10 µl of cAST Ab (1 mg/ml) or mAST Ab (1 mg/ml) and incubated for 1 h at 4° C. Centrifugation was done to remove supernatant, then the pellet was washed with 1× PBS and centrifuged, which was repeated 2 times. The two conjugated protein G-Ab complexes were blocked with milk (5% in 1× PBS) for 1 h at 4° C. and washed described as above. The two complexes were incubated with 200 µl of serum for 12 h while agitating at 4° C. The supernatant was used to test the activity after centrifugation described as above.

4-4. Determination of mAbs Binding to AST Isoenzymes in Serum by Western Blot

Western blot analysis were performed to determine that the present mAbs can recognize AST isoenzymes in serum, and to compare the amount of AST isoenzymes in normal and liver cancer patient serum samples.

4-5. Immunofluorescence Microscopy

HepG2, a liver cancer cell line expressing cAST, was used in this Example. HepG2 cells were grown in complete DMEM containing 10% FBS with 7.0% $CO_2$ supply. For renewal, the culture medium was discarded by a pipette, and added 10 ml of PBS to wash the cells. 3 ml of 0.05% trypsin-EDTA (1×, Invitrogen) was added into the petri dish and cells were treated for 3 min at 37° C. Then the petri dish was shaken gently until most of the cells were detached from the bottom. The cells were collected by centrifugation for 1 min at 1500 rpm. The supernatant was decanted completely and the cells were suspended in 10 ml complete DMEM and transferred into a new petri dish.

Glass coverslips (12 mm circle, Fisher Scientific) were sterilized and placed in 24 well tissue culture plates. HepG2 cells were seeded onto the plate and grown till about 70% confluency. The medium was aspirated from the wells and the cells were rinsed briefly with PBS for 3 times for 5 min each time, and fixed with 4% paraformaldehyde in PBS for 15 min at room temperature. The cells were rinsed three times with PBS for 5 min each, and permeabilized with cold methanol (−20° C.) for 5 min. The cells were blocked with blocking buffer (3% BSA, 0.1% TRITON ™ X-100 (4-(1,1,3,3-Tetramethylbutyl)phenyl-polyethylene glycol) in PBS) and incubated 1 h at room temperature. The coverslips were washed three times with PBS, 5 min each. The primary antibody was diluted with blocking buffer and added to each well and incubated for 1.5 h at room temperature or overnight at 4° C. The coverslips were washed described as above. The fluorochrome-conjugated secondary antibody diluted in blocking buffer was added into each well and incubated for 1 h at room temperature in dark condition, and washed as above. The 4',6-diamidino-2-phenylindole (DAPI, 0.1 µg/ml) was added to each well, incubated for 2 min and washed as above. The coverslip was placed on top of the slides with fluorescent mounting medium (DAKO) and incubated for 1 h at room temperature in dark condition. The fluorescence signal was analyzed under a fluorescence microscopy (Carl Zeiss, EL-Einsatz, Germany).

4-6. Localization of AST Isoenzymes in hepG2 Cell with Western Blot

Figure 4:
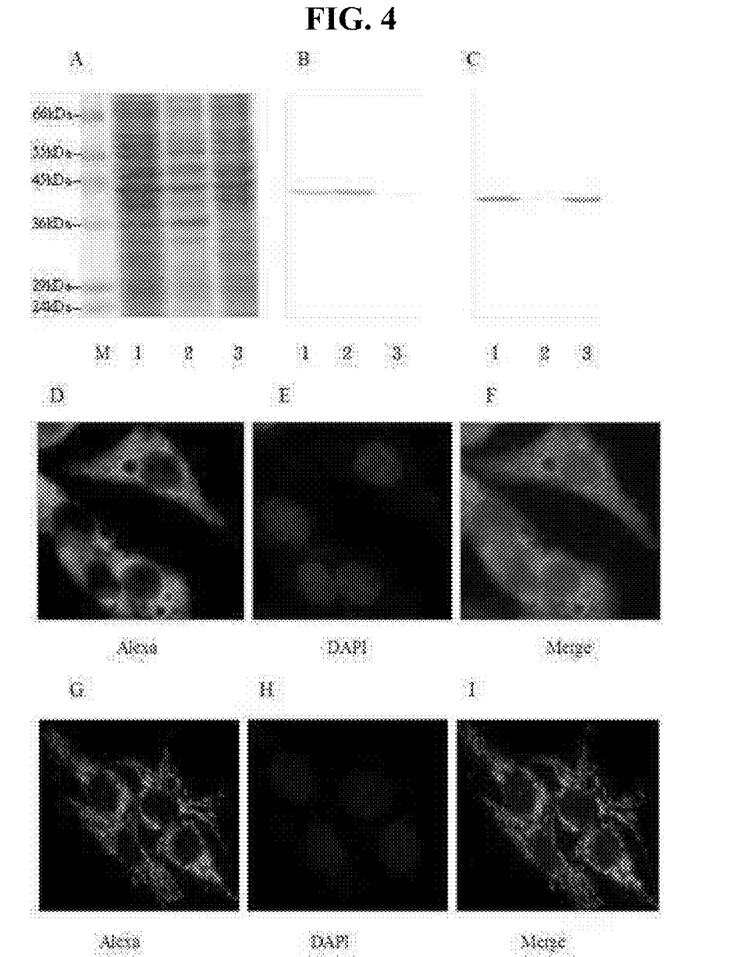
FIG. 4 is the results of analyzing the expression of cAST and mAST in hepG2 cells. The western blot was performed on the whole lysate of hepG2 (Lane 1), the supernatant (Lane 2) and the pellets (Lane 3). (A) is the result of SDS-PAGE. (B) is the result of western blot analysis of cAST using HCC4 as a primary antibody. (C) is the result of western blot analysis of mAST using HCM4 as a primary antibody. D to I are results of immunofluorescence assay performed on hepG2 cells in which HCC4 (D-F) and HCM4 (G-I) were used as primary antibody (1 µg/ml), and FITC conjugates were used as a secondary antibody. In (D) and (G), Alexa was used and in (E) and (H), DAPI was used. In (F) and (I) are the images were merged.

The hepG2 cells were cultured for two days as described above and harvested. Then 200 µl of PBS was added to the cells, which were then homogenized. Half of the whole lysate was then centrifuged at 15000 rpm for 30 min. The supernatant was transferred to a new tube, and the pellet was resuspended with an equal volume of PBS. Then the whole lysate, supernatant and pellet were analyzed by western blot. Results are shown in FIG. 4. As shown in FIG. 4, cAST was detected in cytoplasmic part and mAST in the pellet, which was present in the cytoplasm in the cell staining.

Example 5

Distribution of cAST in Human Liver Tissue

Figure 6:
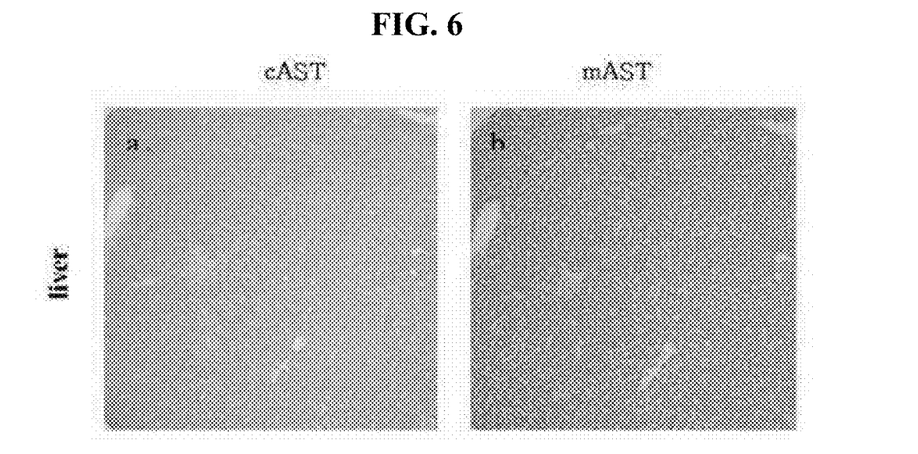
FIG. 6 is the result of analyzing the expression and localization of cAST and mAST in hepatocytes by immunohistochemistry. Magnification: X20.

To localize cAST in human liver tissue, immunohistochemistry was conducted as follows. Commercially available Paraffin-embedded human liver tissue slide was used (Superbiochip co. Ltd, Korea). First, deparaffinization and hydration were performed, the slide was put into xylene and shaken slightly for 5 min under hood, and then transferred into fresh xylene and shaked for 5 min; The slide was hydrated in 100%, 90%, 80% and 70% ethanol for 2 min each, and immersed in tap water for 10 min. The prewarmed pepsin solution (in 37° C. water bath) was added onto each tissue slide for 3 min and rinsed with TBST for 5 times. The peroxidase-blocking solution was added to each slide and incubated for 10 min and rinsed with TBST for 5 times. Then blocking serum was added, incubated for 10 min and rinsed with TBST 5 times. Primary Ab diluted with PBS was then added onto the slide and incubated for 2 hrs. at room temperature or overnight at 4° C., and washed with TBST for 5 times. Secondary Ab conjugated with biotin was then added, and incubated for 10 min and rinsed with TBST 5 times. Avidin-HRP solution was added, incubated for 10 min and rinsed with TBST for 5 times. DAB solution was added, incubated for 30-60 sec, and immersed in tap water to stop reaction. The slide was immersed in hematoxylin for 1 min and incubated while shaking followed by washing with tap water for 10 min. Then the slide was immersed for 1 second in HCl solution (1 ml of original HCl in 1 of 70% ethanol), and washed with tap water for 10 min, then immersed in ammonia for 2 min. The slide was dehydrated in 80%, 90% and 100% ethanol for 2 min each. The slide was rinsed with xylene 2 times, and incubated for 2 min while shaking. After excess xylene was removed with tissue paper, the mounting medium (Abcam) was added onto the tissue and the cover glass was placed onto the tissue. Finally, the slides were examined under a microscope (Sony, Japan). Results are shown in FIG. 6. As shown in FIG. 6, strong cAST reactivity was detected in the hepatocytes.

Example 6

Determination of Amount of AST Isoenzymes in Serum

6-1. Biotinylation of mAbs

To label mAb with biotin, 10 μg of biotin (EZ-Link™ NHS-LC-LC-biotin, Pierce) and 250 μg of mAb were dissolved in 500 μL of PBS. The mixture was incubated for 4 h on ice, and vortexed every half hour. The mixture was then dialyzed against PBS at 4° C.

6-2. Sandwich ELISA

For determine the level of cAST in serum, sandwich ELISA was done as below. 50 μl of mAbs (2 μg/ml) diluted by PBS was applied into EIA plate, and the plate was incubated for 2 h at 37° C. or overnight at 4° C., and washed 3 times with PBST. Blocking buffer was added into each well and incubated for 1 h at 37° C., and washed 3 times with PBST. 50 μl of the recombinant cAST or whole serum were added into each well and incubated for 1 h at 37° C., and washed 3 times with PBST. 50 μl of the biotin-conjugated mAb solution (2 μg/ml) diluted by dilution buffer was added into wells and incubated 1 h at 37° C., and washed 3 times with PBST. 50 μl of Avidin-HRP solution was applied and incubated for 1 h at 37° C., and washed 3 times with PBST. 50 μl of the substrate, TMB was used to develop color and let it stand for 15 min before adding the same volume of stop solution. The OD was read with a microplate reader (wavelength: 450 nm).

Example 7

Measuring the Level of cAST and mAST in Serum Using Immunological Method

7-1. Standard Curve for Measuring cAST and mAST Level

Figure 7:
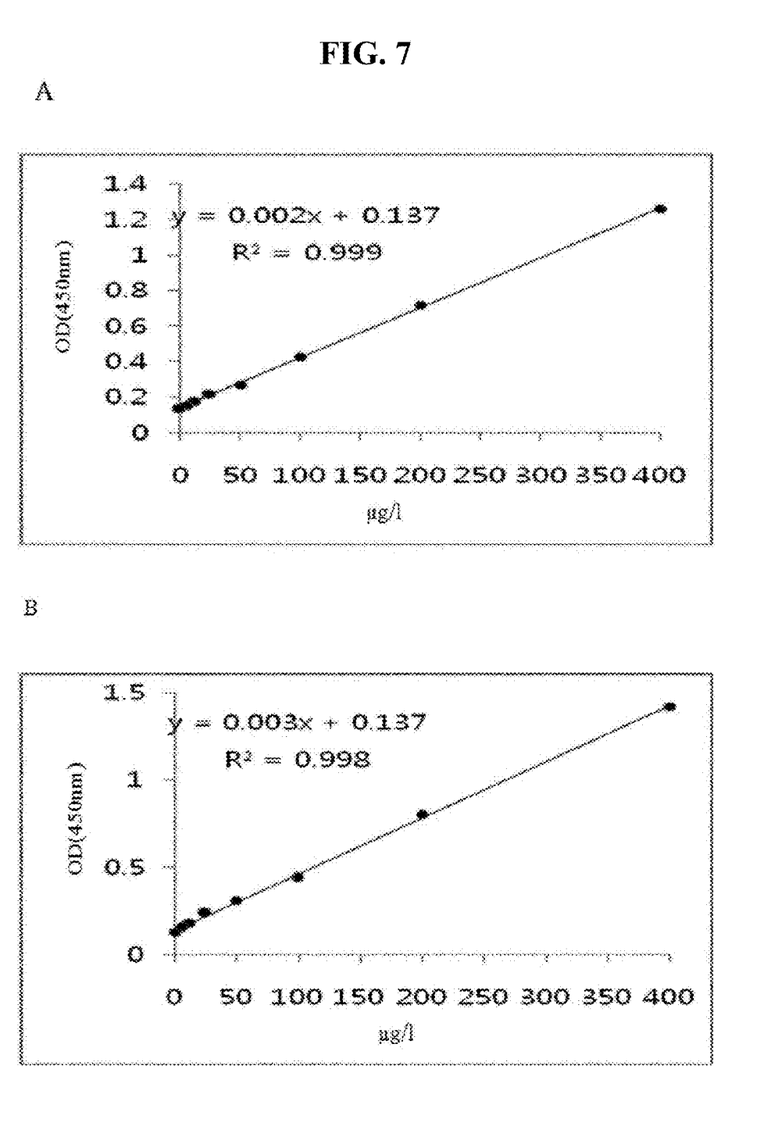

To measure cAST and mAST level in serum samples, standard curves were obtained using different concentrations of the recombinant protein cAST or mAST, from 0 to 400 μg/l of cAST or mAST, by sandwich ELISA system. The healthy normal serum, whose AST enzymatic activity was 10 IU/L, was diluted to 5 times with PBS, spiked with a known concentration of cAST or mAST, and used as calibrator standard serum. In the curve, OD at 450 nm was plotted at the y-axis against the recombinant cAST or mAST concentration at the x-axis. Reliable correlation of coefficients (r: 0.999 and 0.998) were observed between the two parameters, and a good linearity was displayed throughout the entire measuring range (FIG. 7A, B). The coefficient of variations (CVs) of three independent experiments at each concentration was found to be <10%. The imprecision and recovery tests were performed to estimate the analytical performance of the Sandwich ELISA system. For cAST assay system, within-day and between-day imprecision were 2.54-7.15% (tested on 3 samples in 10 replicates) and 3.92-8.34% (tested on 3 samples and assay for consecutive 5 days), respectively, the analytical recovery was found to be 93.1-101.3%. For mAST assay system, within-day and between-day imprecision were 2.95-8.38% (tested on 3 samples in 10 replicates) and 6.52-9.08% (tested on 3 samples and assay for consecutive 5 days), respectively, the analytical recovery was found to be 94.0-103.3%. These results indicate the measuring the level of cAST and mAST using the antibody provides reliable results and thus can be successfully used for clinical sample test.

7-2. Determination of Serum cAST and mAST Level in Healthy Persons and Patients with Liver Disease (1)

Figure 5:
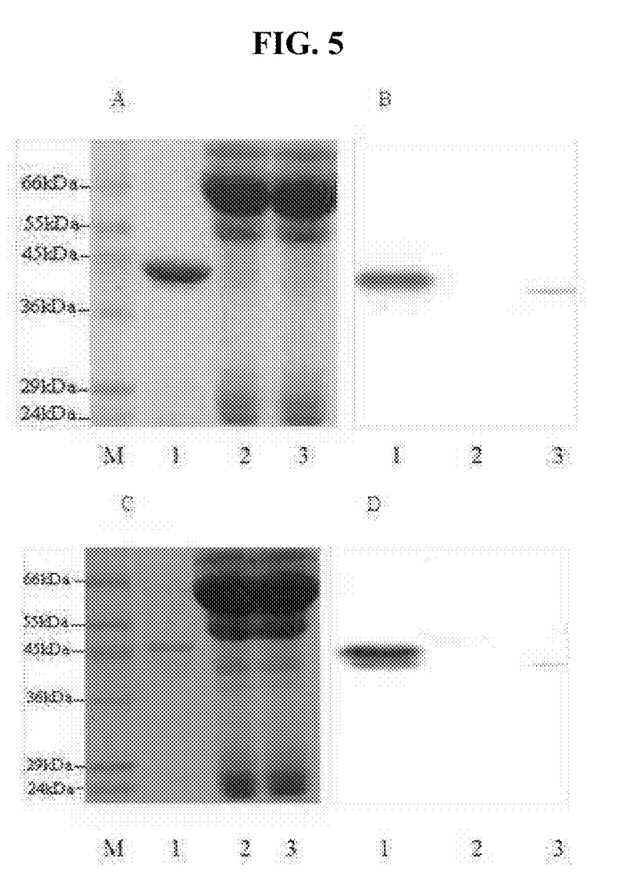
FIG. 5 is the results of analyzing specific binding activity of the present monoclonal antibodies against cAST and mAST to its respective antigen cAST and mAST in serum from normal and liver disease patient sample by electrophoresis (A and B) and western blot (B, D), in which Lanes indicate as follows: 1: recombinant protein; 2: serum from healthy patient (10 IU/L); 3: serum from patient with liver disease (760 IU/L).

When human liver is damaged, cAST and mAST are released into the blood stream. Thus to prove that the released cAST and mAST can be detected in serum with respective antibodies, western blot using the present antibodies were performed. Results are shown in FIG. 5. As shown in FIG. 5, no band was detected in serum from a healthy person. In contrast, the bands corresponding to cAST and mAST were detected in serum from liver cancer patient.

7-3. Determination of Serum cAST and mAST Amount in Healthy Persons and Patients with Liver Disease (2)

After the serum samples were collected from healthy persons and patients with different liver diseases, the level (amount) and the enzymatic activity of serum AST were measured side-by-side using a sandwich immunoassay method and a Hitachi 747 automatic analyzer, respectively. All the serum samples were diluted 5 times with PBS just before the analysis. As shown in Table 2, the mean (SD) of cAST level of healthy control (N=25), CVH (N=24), LC (N=21) and HCC (N=22) were 40.5 (38.6), 228.9 (165.6), 255.3 (154.8) and 327.6 (137.9) μg/l, respectively. The mean (SD) of mAST level of healthy control (N=25), CVH (N=24), LC (N=21) and HCC (N=22) were, respectively, 10.1 (6.1), 11.9 (12.8), 9.7(15.9) and 10.4 (8.7) μg/l. That is, the average level of cAST in healthy normal sample was found to be 40.5±38.6 μg/l. However in CVH, LC and HCC, the average level of cAST was found to be 228.9±165.6 μg/l, 255.3±154.8 μg/l, and 327.6±137.9 μg/l, respectively. The average level of mAST in healthy normal sample was found to be 10.1±6.1 μg/l. However in CVH, LC and HCC, the average level of cAST was found to be 11.9±12.8 μg/l, 9.7±15.9 μg/l, 10.4±8.7 μg/l, respectively. These results indicate that liver disease can be diagnosed by measuring the level of cAST and mAST,

TABLE 2

The level and activities of cAST and mAST in normal control and liver disease patient sample

| Group | Number. | Gender, M/F | Ages | AST, IU/L | cAST μg/l | mAST μg/l |
|---|---|---|---|---|---|---|
| Control | 25 | 14/11 | 48.4 (13.8) | 27.5 (10.9) | 40.5 (38.6) | 10.1 (6.1) |
| CVH | 24 | 14/10 | 44.1 (15.9) | 81 (92.4) | 228.9 (165.6) | 11.9 (12.8) |
| LC | 21 | 20/1 | 51.7 (8.6) | 63.4 (25.4) | 255.3 (154.8) | 9.7 (15.9) |
| HCC | 22 | 15/7 | 57.3 (8.8) | 153.5 (238.2) | 327.6 (137.9) | 10.4 (8.7) |

$^a$Data are represented as the mean (SD) for continuous variables.

7-3. ROC Plot Analysis for cAST in Serum

ROC plot analysis was performed to compare the performance of the present method and conventional enzymatic activity method. For the enzymatic activity test, the enzymatic activity of AST was tested since cAST accounts for 80-90% of total AST in serum and thus would not affect the results.

Figure 8:
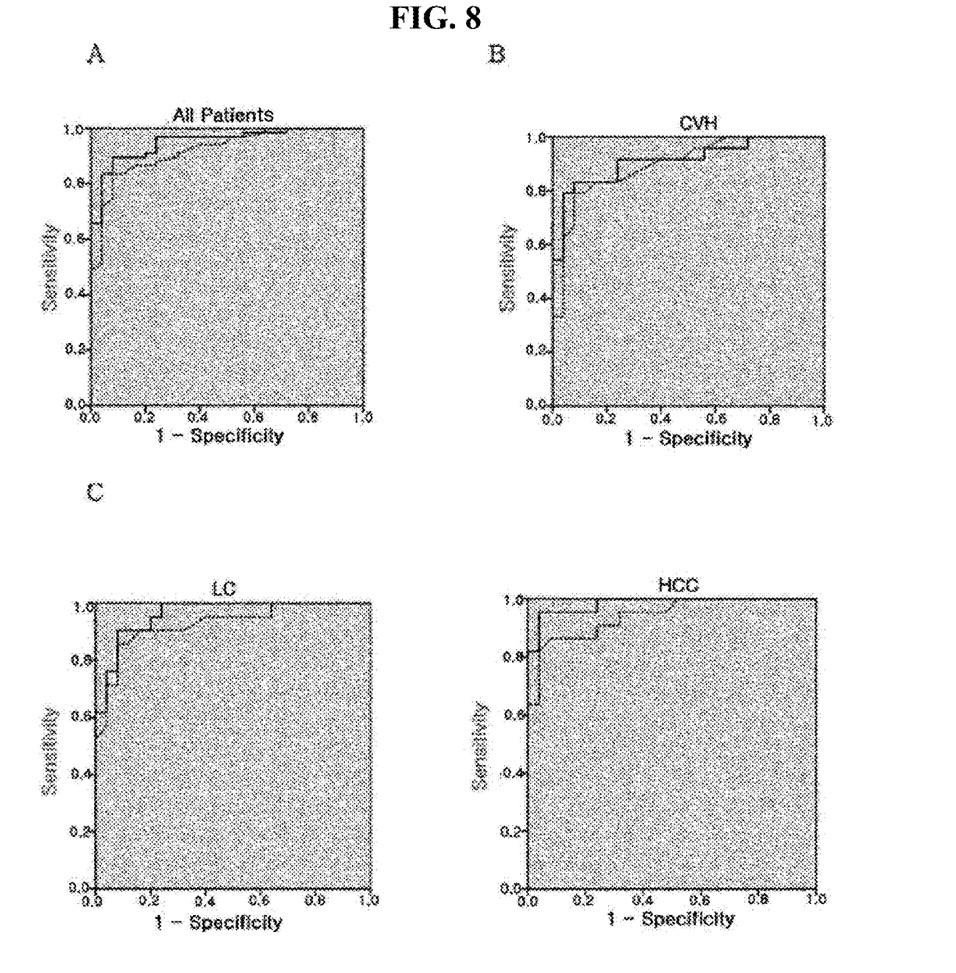
FIG. 8 is a ROC curve obtained with the amount of cAST and enzymatic activity in serum from normal and liver disease patient (Chronic Viral Hepatitis (CVH), LC, and HCC) to compare the specificity and sensitivity of the two methods, one based on the amount of cAST, the other based on the enzymatic activity, in which normal healthy sample and samples from liver disease patient were used. In the figure, (A): all patients' data combined; (B): CVH; (C): LC; and (D): HCC. Black line: the amount of cAST; and dotted line: enzymatic activity of AST.

For this, the level and the enzymatic activity of cAST were analyzed for all the patients combined in one ROC curve or in separate patient groups according to types of liver diseases. Results are shown in Table 3 and FIG. 8. As shown there, the statistical comparison of AUC demonstrated that there were some differences between the two assay methods. The optimal cutoff values for the two assay methods were determined on the basis of the ROC curves. The cutoff values for enzymatic assay method were similar to each other in different patient groups. The cutoff values in the assay for measuring the level, there were no significant change in all the groups except HCC group (108.8 µg/l). With the determined cutoff values, the specificity between measuring the level and the enzymatic activity were found to be identical except HCC group. With regard to sensitivity, the sensitivity of measuring the level was found to be higher than that of enzymatic activity, especially for HCC patient group, in which both of the sensitivity and the specificity showed significant difference between the two methods tested. The sensitivity determined by measuring the level and the enzymatic activity were 0.955 and 0.864, respectively, and the specificity was 0.96 and 0.92, respectively. These results indicate that measuring the level of cAST and/or mAST is more effective than measuring the activity thereof in diagnosing liver disease.

TABLE 3

ROC CURVE ANALYSIS for cAST

| | All patient group | | CVH | | LC | | HCC | |
|---|---|---|---|---|---|---|---|---|
| | amount | activity | amount | activity | amount | activity | amount | activity |
| AUC | 0.952 | 0.921 | 0.913 | 0.897 | 0.962 | 0.928 | 0.984 | 0.942 |
| Cut-off | 82.1 | 39.5 | 84.1 | 39.5 | 82.1 | 40 | 108.8 | 42.5 |
| Sensitivity | 0.896 | 0.836 | 0.833 | 0.79 | 0.905 | 0.857 | 0.955 | 0.864 |
| Specificity | 0.92 | 0.92 | 0.92 | 0.92 | 0.92 | 0.92 | 0.96 | 0.92 |

In table 3, p<0.001 was considered statistically significant.

Example 8

Statistical Analysis

The equation for the standard curve and the correlation of coefficient (r) were obtained using a Microsoft Excel program. The analysis of ROC plot was performed using the Medcalc version 6.12 software program (Medcalc, Mariaekerke, Belgium). Statistical differences between means were calculated using the Student t-test and ANOVA with Bonferroni adjustment. Pearson correlation coefficients and linear regression with the least-squares method were used to evaluate correlations between the patient and control groups. P values <0.05 were considered statistically significant. To assess and compare the diagnostic accuracy of the immunoassay and the enzymatic activity assay of the serum ALT for discriminating in different patients groups with liver diseases, ROC curves were generated by plotting the true positivity (sensitivity) and the false positivity (1-specificity), and were used to calculate cutoff values and the areas under the curves (AUC)

The various singular/plural permutations may be expressly set forth herein for sake of clarity. Although a few embodiments of the present disclosure have been shown and described, it would be appreciated by those skilled in the art that changes may be made in this embodiment without departing from the principles and sprit of the invention, the scope of which is defined in the claims and their equivalents.

Unless defined or interpreted otherwise, all technical and scientific terms and any acronyms used herein have the same meanings as commonly understood by one of ordinary skill in the art in the field of the invention.

Antibody Deposit Information
Depository Institution: Korean Collection for Type Cultures, located 125 Gwahak-ro, Yuseong-gu, Dajeon 305-806, Republic of Korea
Deposit NO (Accession number): KCTC12483BP
Date of Deposit; 2013 Sep. 4
Depository Institution: Korean Collection for Type Cultures, located 125 Gwahak-ro, Yuseong-gu, Dajeon 305-806, Republic of Korea
Deposit NO (Accession number): KCTC12484BP
Date of Deposit: 2013 Sep. 4
Depository Institution: Korean Collection for Type Cultures, located 125 Gwahak-ro, Yuseong-gu, Dajeon 305-806, Republic of Korea
Deposit NO (Accession number): KCTC12485BP
Date of Deposit: 2013 Sep. 4

What is claimed is:

1. A method of quantitatively analyzing at least one of cAST and mAST comprising steps of:
   providing an antibody specific to at least one of cAST and mAST;
   incubating the antibody with a blood sample from a subject; and
   determining the concentration of at least one of the cAST and mAST,
   wherein the antibody is a monoclonal antibody produced by the hybridoma cells deposited as KCTC 12483BP; KCTC 12484BP; or KCTC 12485BP in Korean Collection for Type Cultures.

2. The method of claim 1, wherein the method is performed by a sandwich ELISA.

3. The method of claim 1, wherein the blood sample is whole blood, serum or plasma.

4. The method of claim 1, wherein the subject is one who has a liver disease selected from chronic or acute hepatitis, hepatic cirrhosis and liver cancer.

* * * * *